United States Patent [19]

Torii et al.

[11] Patent Number: 4,665,166
[45] Date of Patent: May 12, 1987

[54] PROCESS FOR PREPARING CEPHALOSPORIN COMPOUNDS

[75] Inventors: Shigeru Torii; Hideo Tanaka; Junzo Nogami, all of Okayama; Michio Sasaoka, Tokushima; Norio Saito, Tokushima; Takashi Shiroi, Tokushima, all of Japan

[73] Assignee: Otsuka Kagaku Kabushiki Kaisha, Osaka, Japan

[21] Appl. No.: 609,080

[22] PCT Filed: Sep. 1, 1983

[86] PCT No.: PCT/JP83/00291
§ 371 Date: May 1, 1984
§ 102(e) Date: May 1, 1984

[87] PCT Pub. No.: WO84/00964
PCT Pub. Date: Mar. 15, 1984

[30] Foreign Application Priority Data

Sep. 2, 1982 [JP] Japan .................. 57-153569

[51] Int. Cl.4 ................................. C07D 501/36
[52] U.S. Cl. ................................. 540/215; 540/26; 540/29
[58] Field of Search .................. 544/16, 26, 29; 540/215, 226, 229

[56] References Cited

U.S. PATENT DOCUMENTS 4,482,491 11/1984 Torii, II .................. 544/26

OTHER PUBLICATIONS

Torii-I, Tetrahedron Letters 23(24), pp. 2495–2498, 1982.
Franceschi, Journal of the American Chemical Society, 99(1), pp. 248–250 (1977).

Primary Examiner—Sidney Marantz
Assistant Examiner—Robert Benson
Attorney, Agent, or Firm—Armstrong, Nikaido, Marmelstein & Kubovcik

[57] ABSTRACT

A process for preparing cephalosporin compounds represented by the formula

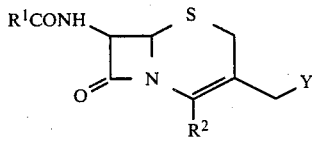

wherein $R^1$ represents an alkyl group, alkenyl group, substituted or unsubstituted aryl group, substituted or unsubstituted arylmethyl group or substituted or unsubstituted phenoxymethyl group, $R^2$ represents a carboxyl group or protected carboxyl group, and Y represents the residue of a nucleophilic reagent.

3 Claims, No Drawings

PROCESS FOR PREPARING CEPHALOSPORIN COMPOUNDS

TECHNICAL FIELD AND DISCLOSURE OF THE INVENTION

This invention relates to a process for preparing cephalosporin compounds, and more particularly to a process for preparing cephalosporin compounds represented by the formula

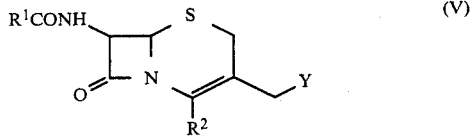

wherein $R^1$ represents an alkyl group, alkenyl group, substituted or unsubstituted aryl group, substituted or unsubstituted arylmethyl group or substituted or unsubstituted phenoxymethyl group, $R^2$ represents a carboxyl group or protected carboxyl group, and Y represents the residue of a nucleophilic reagent.

The cephalosporin compounds of the formula (V) have antibacterial activity and thus are useful as antibacterial agents. The compounds can be converted into cephalosporin type antibiotics in wide use by deacylating and reacylating the amide group at the 7-position and thus are important intermediates for synthesizing such antibiotics.

An object of the present invention is to provide a process for preparing the cephalosporin compounds of the formula (V) with high purities in high yields by a simple procedure from inexpensive and readily available starting compounds.

Examples of the alkyl groups represented by $R^1$ in the formula (V) are methyl, ethyl, propyl, isopropyl, buty, tert-butyl and like lower alkyl groups having 1 to 4 carbon atoms. Examples of the alkenyl groups represented by $R^1$ are allyl, butenyl, hexenyl and like lower alkenyl groups having 2 to 6 carbon atoms. Examples of the aryl groups represented by $R^1$ are phenyl, naphthyl and the like. Examples of the substituted aryl groups represented by $R^1$ are phenyl groups having as substituents lower alkyl, halogen, nitro, lower alkyloxy or the like on the aromatic ring, such as tolyl, xylyl, p-chlorophenyl, p-nitrophenyl, p-methoxyphenyl, etc. Examples of the arylmethyl groups represented by $R^1$ are benzyl, naphthylmethyl, etc. Examples of the substituted arylmethyl groups represented by $R^1$ are phenylmethyl groups having as substituents lower alkyl, halogen, nitro, lower alkyloxy or the like on the phenyl ring, such as tolylmethyl, p-chlorophenylmethyl, p-nitrophenylmethyl, p-methoxyphenylmethyl, etc. Examples of the substituted or unsubstituted phenoxymethyl groups represented by $R^1$ are phenoxymethyl, and phenoxymethyl groups having as substituents lower alkyl, halogen, nitro, lower alkyloxy or the like on the phenyl ring, such as tolyloxymethyl, p-chlorophenoxymethyl, p-nitrophenoxymethyl, p-methoxyphenoxymethyl, etc.

Examples of the protected carboxyl groups represented by $R^2$ are esters of the formula COOR' and acid amides of the formula CONHR' etc. Examples of the groups represented by R' in the foregoing formulae are methyl, 2,2,2-trichloroethyl, diphenylmethyl, benzyl, p-nitrobenzyl, isobutyl, tert-butyl or like carboxylic acid-protecting groups commonly used.

Examples of the residues of nucleophilic reagents represented by Y include groups

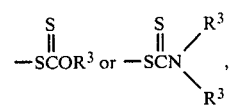

groups $-SR^4$, hydroxyl group, protected hydroxyl group, nitroxy group ($-ONO_2$), etc. Examples of the groups represented by $R^3$ are lower alkyl groups having 1 to 4 carbon atoms and optionally substituted with halogen, such as methyl, ethyl, propyl, isopropyl, butyl, tert-butyl, etc.; phenyl group; phenyl groups substituted with lower alkyl, halogen, nitro, lower alkyloxy or the like, such as tolyl, p-chlorophenyl, p-nitrophenyl, p-methoxyphenyl; etc. Examples of the groups represented by $R^4$ are the same as those represented by $R^3$ or substituted or unsubstituted residues of the aromatic heterocyclic ring, such as the following groups:

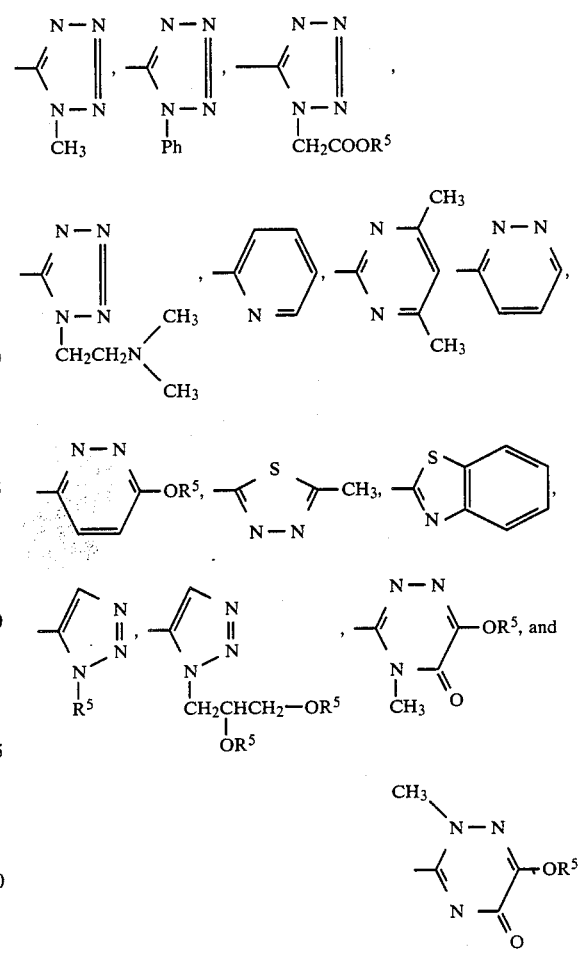

Examples of the groups represented by $R^5$ are hydroxyl-, carboxyl- and amine-protecting groups, such as methyl, ethyl, propyl or like lower alkyl groups. Examples of the protected hydroxyl groups are groups

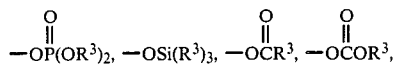

etc. wherein $R^3$ is as defined above.

According to the present invention, the cephalosporin compounds of the formula (V) can be prepared as follows.

First, a thiazolinoazetidinone derivative of the formula

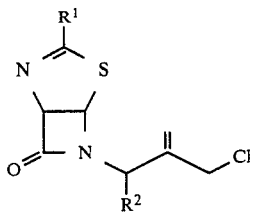

(I)

wherein $R^1$ and $R^2$ are as defined above is reacted with a nucleophilic reagent by a method to be described later to introduce the residue of the nucleophilic reagent without altering the position of the double bond, whereby a thiazolinoazetidinone derivative of the formula

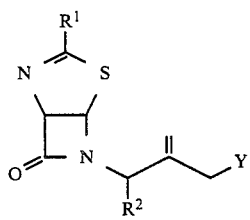

(II)

wherein $R^1$, $R^2$ and Y are as defined above is obtained.

Subsequently the compound of the formula (II) is reacted in a water-containing solvent with a sulfur-containing compound of the formula

Z—S—X (III)

wherein Z represents a substituted or unsubstituted aryl group or the residue of the substituted or unsubstituted aromatic heterocyclic ring and X represents a halogen atom, whereby an azetidinone derivative of the formula

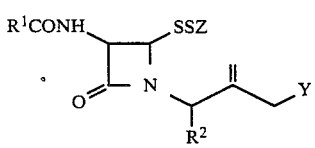

(IV)

wherein $R^1$, $R^2$, Y and Z are as defined above is obtained.

Thereafter ammonia is added to the compound of the formula (IV) to subject the compound to the action of the ammonia in an organic solvent, whereby the compound of the formula (V) is produced.

The compound of the formula (I) to be used as the starting material in the present invention can be easily synthesized for example from a known thiazolinoazetidinone derivative of the formula

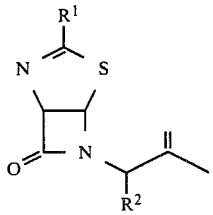

(VII)

wherein $R^1$ and $R^2$ are as defined above by a conventional method, for instance, as disclosed in Tetrahedron Letters, 22, 3193 (1981).

The compound of the formula (II) serving as the intermediate in the present invention is prepared by reacting the starting compound of the formula (I) with a nucleophilic reagent. Essentially this reaction is conducted to replace the chlorine atom at the allyl position by the nucleophilic reagent without changing the position of the C=C double bond of the compound having the formula (I), thereby giving the compound of the formula (II).

There has been reported a process for synthesizing the compound of the formula (II) (wherein $R^1$ is methyl or tert-butyl, $R^2$ is a group COOCH$_3$ and Y is a group

which process involves a number of procedures [J. Am. Chem. Soc., 99, 248 (1977)], as shown in the following reaction equation.

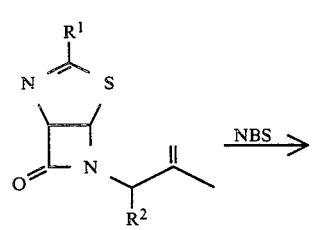

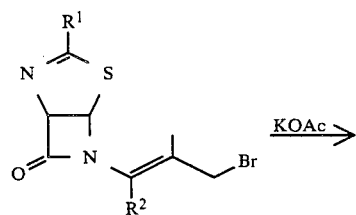

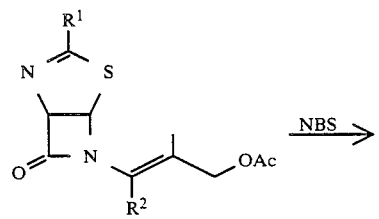

-continued

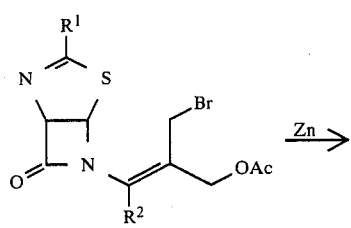

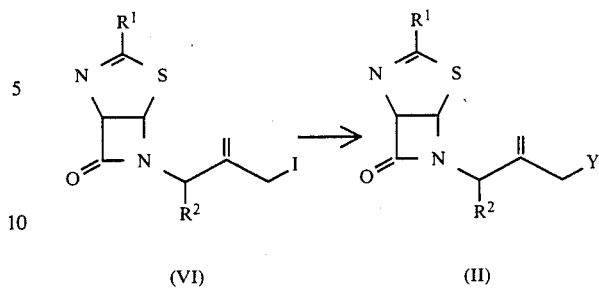

(VI)      (II)

Reaction Equation (C)

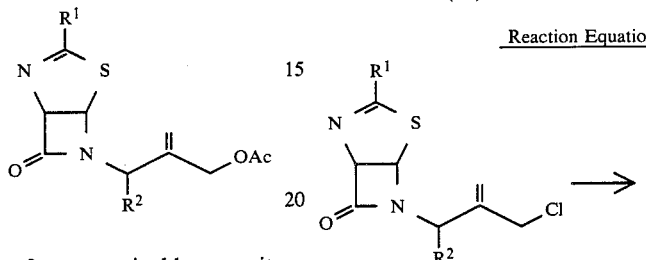

(I)

However, this process is far from practical because it has the drawbacks of using N-bromosuccinimide (NBS) or like expensive reactants, requiring a number of procedures due to change in the position of the double bond and giving an end product in low yields.

On the other hand, the process of the present invention can provide the compound of the formula (II) in high yields by a simple procedure (or procedures) without involving the movement of the double bond.

According to the present invention, the compound of the formula (I) can be made into the compound of the formula (II) by any of processes as illustrated hereinafter by reaction equations (A) to (C).

Reaction Equation (A)

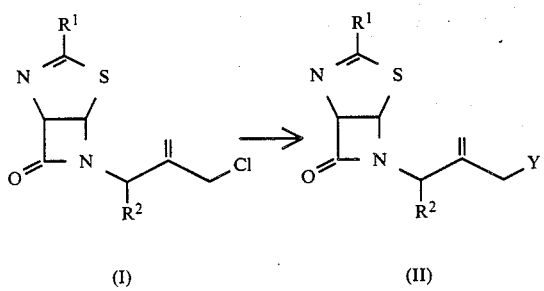

(I)      (II)

Reaction Equation (B)

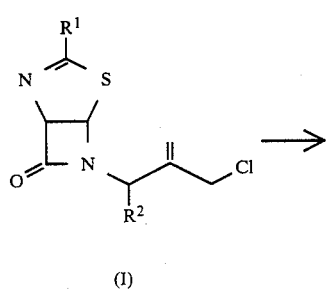

(I)

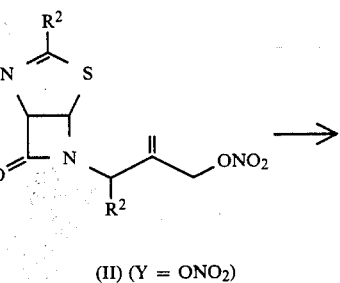

(VI)

(II) (Y = ONO$_2$)

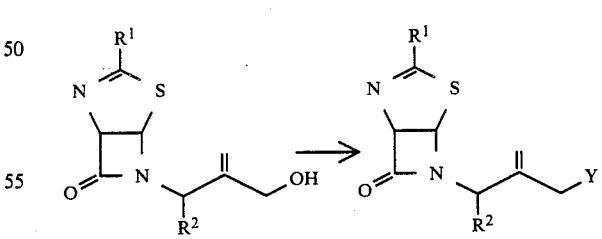

(IX)      (II)

(1) The process as shown by the reaction equation (A) is especially advantageous in preparing the compound of the formula (II) wherein Y is a group $$-\overset{\overset{\text{S}}{\|}}{\text{SC}}\text{OR}^3$$

(in which $R^3$ is as defined above). More specifically, the compound of the formula (II) wherein Y is the group

can be prepared in a high yield without varying the position of the double bond by reacting the compound of the formula (I) in an organic solvent with a nucleophilic reagent represented by the formula

 (1)

wherein M is an alkali metal and $R^3$ is as defined above. The nucleophilic reagent of the formula (1) is a known compound which is preferably used in the form of sodium salt or potassium salt. The kind of the organic solvent to be used in this reaction is not particularly limited so far as the solvent is capable of dissolving the compound of the formula (I) and the nucleophilic reagent. Preferred examples of useful organic solvents are acetone, ethyl acetate, dimethyl sulfoxide, dimethylformamide and like aprotic polar solvents. The amount of the organic solvent to be used is not particularly limited insofar as the amount is sufficient to dissolve the reactants. The solvent is used in an amount of usually about 5 to about 100 times, preferably about 5 to about 50 times, the weight of the compound of the formula (I). The amounts of the starting compound of the formula (I) and the nucleophilic reagent of the formula (1) to be used can be also adequately determined over a wide range. The latter is employed in an amount of usually about 1 to about 10 moles, preferably about 1 to about 5 moles, per mole of the former. The reaction is conducted at a temperature in the range of usually about $-10°$ to about 40° C., preferably at room temperature and is completed usually in 0.5 to 2 hours.

(2) The process as shown by the reaction equation (B) is particularly advantageous in producing the compound of the formula (II) wherein Y is a group

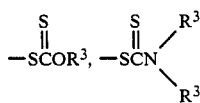

(wherein $R^3$ is as defined above) or $-SR^4$ (wherein $R^4$ is as defined above).

More specifically stated, first the compound of the formula (I) serving as the starting material is reacted in an organic solvent with an alkali iodide, preferably sodium iodide or potassium iodide, whereby a compound of the formula

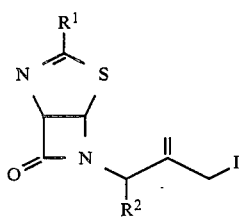 (VI)

wherein $R^1$ and $R^2$ are as defined above is obtained without involving the change in the position of the double bond. Subsequently the compound of the formula (VI) is reacted in an organic solvent with a nucleophilic reagent of the formula

 M—Y (2)

(wherein M is an alkali metal, Y is a group

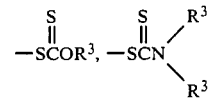

(or $-SR^4$ and $R^3$ and $R^4$ are as defined above), whereby the compound of the formula (II) is obtained in a high yield without changing the position of the double bond.

The organic solvents useful in the reaction between the starting compound of the formula (I) and the alkali iodide include a wide variety of those which are capable of dissolving the two materials. Preferred solvents are aprotic polar ones, such as acetone, dimethyl sulfoxide, dimethylformamide, etc. among which acetone is particularly preferable to use. The amount of the organic solvent to be used is about 5 to about 100 times, preferably 5 to 50 times, the weight of the starting compound of the formula (I). The amounts of the starting compound of the formula (I) and the alkali iodide to be employed can be appropriately determined over a wide range. The latter is used in an amount of usually about 1 to about 10 moles, preferably about 1 to 2 moles, per mole of the former. The reaction is performed at a temperature of usually about 0° to about 60° C., preferably about 40° to about 55° C., and is completed usually in 0.5 to 4 hours.

Examples of the organic solvent which can be used in the reaction between the compound of the formula (VI) and the nucleophilic reagent of the formula (2) include a wide variety of organic solvents capable of dissolving the two compounds among which it is preferred to use aprotic polar solvents, such as acetone, dimethyl sulfoxide, dimethylformamide, etc. and acetone is especially preferable. The organic solvent is employed in an amount of usually about 5 to about 100 times, preferably about 5 to about 50 times, the weight of the compound of the formula (VI). The amounts of the compounds of the formula (VI) and the nucleophilic reagent to be used can be suitably determined over a wide range. The latter is used in amount of usually about 1 to about 3, preferably about 1 to about 1.5 moles, per mole of the former. The reaction is effected at a temperature of usually about $-10°$ to about 40° C., preferably at room temperature and is completed usually in about 0.5 to about 4 hours.

(3) The compound of the formula (II) wherein Y is $-ONO_2$ can be prepared also by the process of the reaction equation (B). More specifically stated, the iodine compound of the formula (VI) which can be produced for example by the process described above in (2) is reacted in an organic solvent with a nitrate of alkali metal, preferably $NaNO_3$ or $KNO_3$, whereby the compound of the formula (II) wherein Y is a nitroxy group is given in a high yield without change in the position of the double bond. Useful organic solvents include aprotic polar solvents among which dimethyl sulfoxide is particularly preferred. The organic solvent is used in an amount of about 0.5 to about 10 times, preferably about 0.5 to about 5 times, the weight of the compound of the formula (VI). The amounts of the compound of the formula (VI) and the nitrate of alkali metal to be used can be appropriately determined over a wide range. The latter is used in a amount of usually about 1 to about 10 moles, preferably about 1 to about 5 moles, per mole of the former. The reaction is carried out at a temperature of usually about 0° to about 100° C., preferably about 40° to about 60° C. In order to remove the alkali iodide produced as a by-product from the reaction system, the reaction can be conducted in the presence of methyl methanesulfonate or methyl toluene sulfonate with the reaction system maintained at reduced pressure of about 30 to about 80 mmHg. Although depending on the reaction conditions, the reaction is completed usually in about 0.5 to about 6 hours.

(4) The compound of the formula (II) wherein Y is a hydroxyl group or a protected hydroxyl group can be produced particularly with advantage according to the reaction equation (C). More specifically, the compound of the formula (II) wherein Y is —ONO$_2$ and which can be prepared by the process described above in (3) is reacted in the presence of acetic acid with zinc to provide a compound of the formula

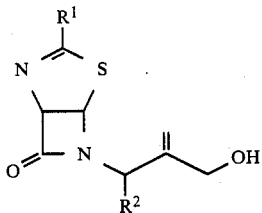

(IX)

wherein $R^1$ and $R^2$ are as defined above. In this reaction, the acetic acid may be used itself as a solvent or in mixture with another organic solvent. Useful organic solvents include a broad range of those inert to acetic acid, zinc and the compound of the formula (II) wherein Y is —ONO$_2$, such as ethyl acetate, methyl acetate, methyl propionate or like lower alkyl esters of lower carboxylic acid; diethyl ether, tetrahydrofuran, dioxane or like ethers; methylene chloride, dichloroethane, chloroform or like halogenated hydrocarbons; benzene, toluene, xylene and like aromatic hydrocarbons, etc. These inert organic solvents are used in an amount of up to about 90%, preferably about 20 to about 70%, based on the volume of the mixture with acetic acid. When singly used or mixed with another organic solvent, the acetic acid is employed in an amount of usually about 10 to about 200 moles, preferably about 10 to about 150 moles, per mole of the compound of the formula (II) wherein Y is —ONO$_2$. The amounts of the compound of the formula (II) wherein Y is —ONO$_2$ and zinc to be used can be suitably selected over wide range. Usually about 3 to about 10 moles, preferably about 3 to about 5 moles of the latter is used per mole of the former. The reaction is carried out at a temperature of usually about −30° to about 50° C., preferably about −10° to about 30° C. and is completed usually in about 0.5 to about 3 hours.

The procedure for protecting the hydroxyl group of the compound of the formula (IX) thus prepared is subsequently conducted, whereby the compound of the formula (II) wherein Y is a protected hydroxyl group can be produced in a high yield. The protection of hydroxyl group is performed by reacting the compound of the formula (IX) with an agent for introducing the corresponding protecting group, such as

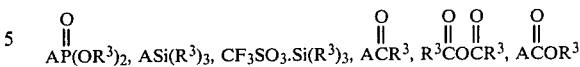

(in the formulae, $R^3$ is as defined above and A is chlorine, bromine or iodine atom). The reaction is conducted usually in an organic solvent in the presence of an acid-trapping agent. Useful acid-trapping agents include pyridine, polymer-supported pyridine, molecular sieve, imidazole, etc. The reaction is effected preferably at a relatively low temperature usually ranging from about −50° to about 10° C. The amounts of the compound of the formula (IX) and acid-trapping agent to be used can be appropriately determined over a wide range. The latter is used in an amount of usually about 1 to about 30 moles, preferably about 1 to about 10 moles, per mole of the former. While the amounts of the compound of the formula (IX) and the agent for introducing a protecting group to be used are variable depending on the kind of the agent, the other reaction conditions, etc., the latter is used in an amount of usually about 1 to about 30 moles, preferably about 1 to about 10 moles, per mole of the former. Useful organic solvents include a wide variety of solvents inert under the foregoing reaction conditions, such as diethyl ether, tetrahydrofuran, dioxane and like ethers; methylene chloride, dichloroethane, chloroform and like haloganated hydrocarbons; benzene, toluene, xylene and like aromatic hydrocarbons; etc. The amount of these organic solvents to be used is about 1 to about 20 times, preferably about 1 to about 15 times, the weight of the compound of the formula (IX). The reaction takes usually 0.5 to 12 hours.

The compound of the formula (II) prepared by any of the processes described above in (1) to (4) is reacted with a sulphur-containing compound represented by the formula

Z—S—X (III)

wherein Z is a substituted or unsubstituted aryl group or residue of the substituted or unsubstituted aromatic heterocyclic ring and X is a halogen atom to obtain the compound of the formula (IV).

Examples of the substituted or unsubstituted aryl groups represented by Z are phenyl, phenyl substituted with halogen, nitro or the like, such as p-nitrophenyl, pentachlorophenyl, trichlorophenyl, etc. Examples of the residues of the substituted or unsubstituted aromatic heterocyclic ring represented by Z are 2-pyridyl, 2-benzothiazolyl, 1,3,4-thiadiazole-2-yl, 5-methyl-1,3,4-thiadiazole-2-yl, etc. Examples of the halogen atoms represented by X are chlorine, bromine, iodine and the like among which chlorine is particularly preferred.

The reaction between the compound of the formula (II) and the sulphur-containing compound of the formula (III) is conducted in a water-containing organic solvent. Usable as the organic solvent are dimethyl sulfoxide, dioxane, tetrahydrofuran, etc. These solvents are used in an amount of usually about 5 to about 50 times, preferably about 5 to about 30 times, the weight of the compound of the formula (II). Although suitably selectable over a wide range, the usual water content in the organic solvent is about 1 to about 500 moles, preferably about 10 to about 100 moles, per mole of the compound of the formula (II). While the amounts of the compounds of the formulae (II) and (III) to be used can be adequately determined over a wide range, the latter is used in an amount of usually about 1 to about 10 moles, preferably about 1 to about 4 moles, per mole of the former. The reaction is conducted at a temperature of usually about −10° to about 60° C., preferably at room temperature of usually about −10° to about 60° C., preferably at room temperature and is completed usually in about 0.1 to about 2 hours. In this reaction, the presence of an inorganic acid or organic acid may increase the yield. Preferred inorganic acids are sulfuric acid, hydrochloric acid, perchloric acid, etc. and preferred organic acids are trifluoroacetic acid, p-toluenesulfonic acid, etc. The amount of these acids to be used is about 1 to about 10 moles per mole of the compound of the formula (II).

The sulphur-containing compound of the formula (III) can be prepared by dissolving the corresponding disulfide or thiol in an inert solvent such as carbon tetrachloride, chloroform, methylene chloride, dioxane, tetrahydrofuran or the like and reacting the solution with molecular halogen. In this reaction the inert solvent is used usually in an amount of about 5 to about 50 times the weight of the disulfide or thiol. The molecular halogen is employed usually in an amount of about 1 to about 1.5 moles per mole of the disulfide or thiol. The reaction favorably proceeds at a temperature of 0° to 100° C. and is completed usually in about 0.5 to about 5 hours. The compound of the formula (III) thus prepared may be subjected to the subsequent reaction as mixed with or as isolated from the reaction mixture.

The compound of the formula (IV) prepared by the reaction between the compounds of the formulae (II) and (III) is converted to the end product of the formula (V) by reacting the ammonia in an organic solvent. Preferred organic solvents are inert aprotic polar solvents such as dimethylformamide, dimethylacetamide, etc. among which dimethylformamide is more preferable. The amount of these organic solvents to be used is about 1 to about 100 times, preferably about 1 to about 50 times, the weight of the compound of the formula (IV). The amounts of the compound of the formula (IV) and the ammonia to be used can be suitably determined over a wide range. The latter is used in an amount of usually about 1 to about 10 moles, preferably about 1 to about 3 moles, per mole of the former. The reaction is conducted at a temperature of usually about −78° to about 20° C., preferably about −40° to about 5° C. and is completed usually in about 0.1 to about 2 hours.

The foregoing process gives the compound of the formula

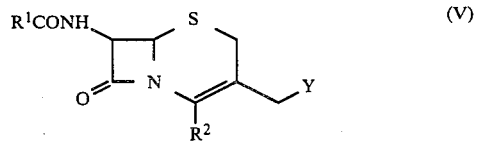

wherein $R^1$, $R^2$ and Y are as defined above.

The compound of the formula (V) wherein Y is —ONO$_2$ [hereinafter referred to as compound (X)] can be made into a compound of the following formula (XI) by reacting with zinc in the presence of acetic acid

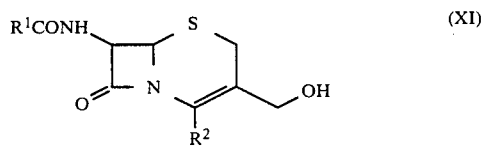

wherein $R^1$ and $R^2$ are as defined above.

The cephalosporin compound of the formula (XI) has an antibacterial activity and is useful as an antibacterial agent. The cephalosporin compound of the formula (XI) is an important intermediate for synthesizing a cephalosporin-type antibiotic into which the compound of the formula (XI) can be converted by introducing a protective group in a conventional manner to change the hydroxyl group into one of various ether groups or ester groups such as esters of carboxylic acid and inorganic acid or by deacylation or reacylation of the amide group at the 7-position.

The amount of the acetic acid which is used in the reaction for preparing the compound of the formula (XI) by subjecting the compound of the formula (X) to the action of zinc in the presence of acetic acid is not particularly limited and can be suitably selected over a wide range. The acetic acid is used usually as a solvent or preferably in mixture with another organic solvent. The organic solvent is employed in an amount of up to about 90%, preferably about 20 to about 70%, based on the volume of the mixture. When singly used or mixed with an organic solvent, the acetic acid is employed in an amount of usually about 10 to about 200 moles, preferably about 10 to about 150 moles, per mole of the compound of the formula (X). The amounts of the compound of the formula (X) and zinc to be used are not particularly limited and can be selected over a wide range. The zinc is used in an amount of usually about 3 to about 10 moles, preferably about 3 to about 5 moles, per mole of the compound of the formula (X). The reaction is carried out at a temperature of usually −30° to 50° C., preferably −10° to 30° C. Examples of the organic solvent to be used as mixed with acetic acid include a wide variety of those inert to acetic acid and zinc under the above conditions, such as ethyl acetate, methyl acetate, methyl propionate and like esters; diethyl ether, tetrahydrofuran, dioxane and like ethers; methylene chloride, dichloroethane, chloroform and like halogenated hydrocarbons; benzene, toluene, xylene and like aromatic hydrocarbons; etc. The reaction is completed usually in about 0.2 to about 3 hours.

The compounds of the formulae (VI), (II) and (IV) prepared by the above reactions may be subjected to the subsequent reaction as mixed with or as isolated from the reaction mixture. The compound of the formula (V) eventually obtained can be purified by solvent extraction, column chromatography, recrystallization or like conventional method.

Examples are given below to describe in more detail the processes of the present invention. In the examples, Ph is used to mean a phenyl group.

EXAMPLE 1

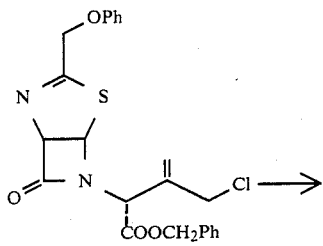

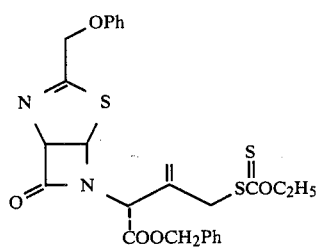

A 1 ml quantity of acetone was added to 37.2 mg of benzyl 2-(3-phenoxymethyl-7-oxo-4-thia-2,6-diazabicyclo[3,2,0]hepto-2-ene-6-yl)-3-chloromethyl-3-butenate to obtain a uniform solution.

(35.2 mg) was added to the solution. The mixture was stirred at room temperature for 70 minutes and diluted with 5 ml of ethyl acetate and the dilute solution was washed with a saturated aqueous solution of sodium chloride, dried over $Na_2SO_4$ and concentrated. The colorless oily residue thus obtained was subjected to silica gel column chromatography by using benzene and then benzene/ethyl acetate (30:1), giving 34.7 mg of benzyl 2-(3-phenoxymethyl-7-oxo-4-thia-2,6-diazabicyclo[3,2,0]hepto-2-ene-6-yl)-ethoxythiocarbonylthiomethyl-3-butenate in 79% yield.

NMR (δ, CDCl₃); 1.35 (t, 3H, 7 Hz), 3.80 (s, 2H), 4.60 (q, 2H, 7 Hz), 4.90 (s, 2H), 5.06 (s, 2H), 5.16 (s, 1H), 5.37 (s, 1H), 5.86 and 6.00 (ABq, 2H, 4 Hz), 6.7–7.4 (m, 5H), 7.32 (s, 5H).

EXAMPLE 2

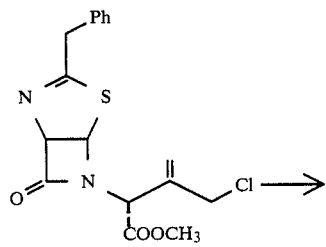

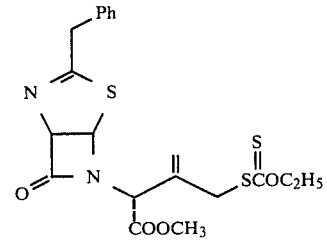

A 1 ml quantity of acetone was added to 21.4 mg of methyl 2-(3-benzyl-7-oxo-4-thia-2,6-diazabicyclo[3,2,0]hepto-2-ene-6-yl)-3-chloromethyl-3-butenate to obtain a uniform solution. To the mixture was added 25.4 mg of

and the resulting admixture was stirred at room temperature for 60 minutes. The reaction mixture was diluted with 5 ml of dimethyl ether and the dilute solution was washed with a saturated aqueous solution of sodium chloride, dried over $Na_2SO_4$ and concentrated. The pale yellow oily residue thus obtained was subjected to silica gel column chromatography by using benzene/ethyl acetate (10:1), giving 22.8 mg of methyl 2-(3-benzyl-7-oxo-4-thia-2,6-diazabicyclo[3,2,0]-hepto-2-ene-6-yl)-3-ethoxythiocarbonylthiomethyl-3-butenate in 86% yield.

NMR (δ, CDCl₃); 1.39 (t, 3H, 7 Hz), 3.70 (s, 5H), 3.87 (s, 2H), 4.63 (q, 2H, 7 Hz), 5.00 (s, 1H), 5.07 (s, 1H), 5.34 (s, 1H), 5.87 (bs, 2H), 7.25 (s, 5H).

EXAMPLE 3

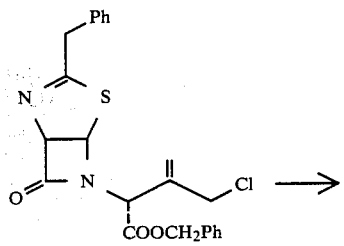

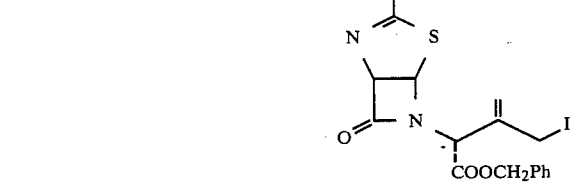

A 1.2 ml quantity of acetone was added to 94.6 mg of benzyl 2-(3-benzyl-7-oxo-4-thia-2,6-diazabicyclo[3,2,0]hepto-2-ene-6-yl)-3-chloromethyl-3-butenate to obtain a uniform solution. To the solution was added 64.3 mg of NaI and the mixture was heated to 55° C. while being stirred for 1.5 hours. The reaction mixture was cooled to room temperature and diluted with 5 ml of ethyl acetate. The dilute solution was washed with an aqueous solution of $Na_2S_2O_3$ and then a saturated aqueous solution of sodium chloride, dried over Na$_2$SO$_4$ and concentrated, affording 113.0 mg of benzyl 2-(3-benzyl-7-oxo-4-thia-2,6-diazabicyclo[3,2,0]hepto-2-ene-6-yl)-3-iodomethyl-3-butenate as a colorless oil in 99% yield.

NMR (δ, CDCl$_3$); 3.63 (s, 2H), 3.83 (s, 2H), 4.95 (s, 1H), 5.17 (s, 2H), 5.23 (s, 2H), 5.38 (s, 1H), 5.87 (bs, 2H), 7.26 (s, 5H), 7.33 (s, 5H).

EXAMPLE 4

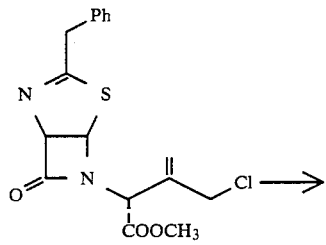

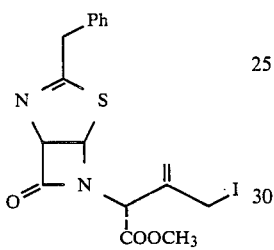

A 10 ml quantity of acetone was added to 376 mg of methyl 2-(3-benzyl-7-oxo-4-thia-2,6-diazabicyclo[3,2,0]hepto-2-ene-6-yl)-3-chloromethyl-3-butenate to obtain a uniform solution. To the solution was added 230 mg of NaI and the resulting mixture was heated to 55° C. while being stirred for 3 hours.

The reaction mixture was cooled to room temperature and diluted with ethyl acetate. The dilute solution was washed with an aqueous solution of Na$_2$S$_2$O$_3$ and then a saturated aqueous solution of sodium chloride, dried over Na$_2$SO$_4$ and concentrated. The pale yellow oily residue thus obtained was subjected to silica gel column chromatography, using hexane/ethyl acetate (4:1), giving 425 mg of methyl 2-(3-benzyl-7-oxo-4-thia-2,6-diazabicyclo-[3,2,0]hepto-2-ene-6-yl)-3-iodomethyl-3-butenate in 90% yield.

NMR (δ, CDCl$_3$); 3.62 (bs, 2H), 3.74 (s, 3H), 3.87 (bs, 2H), 5.04 (s, 1H), 5.21 (s, 1H), 5.91 (bs, 2H), 7.27 (s, 5H).

EXAMPLE 5

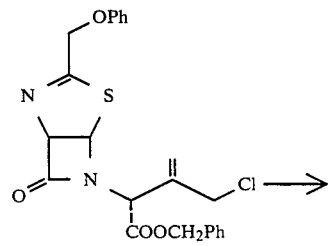

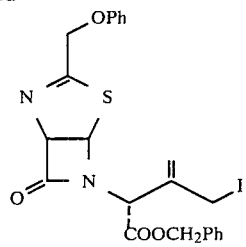

A 10 ml quantity of acetone was added to 374 mg of benzyl 2-(3-phenoxymethyl-7-oxo-4-thia-2,6-diazabicyclo[3,2,0]hepto-2-ene-6-yl)-3-chloromethyl-3-butenate to obtain a uniform solution. To the solution was added 154 of NaI and the mixture was heated to 55° C. while being stirred for 3 hours. The reaction mixture was cooled to room temperature and the mixture was diluted with ethyl acetate. The dilute solution was washed with an aqueous solution of Na$_2$S$_2$O$_3$ and then a saturated aqueous solution of sodium chloride, dried over Na$_2$SO$_4$ and concentrated. The pale yellow oily residue thus prepared was subjected to silica gel column chromatography by using benzene/ethyl acetate (30:1), giving 359 mg of benzyl 2-(3-phenoxymethyl-7-oxo-4-thia-2,6-diazabicyclo[3,2,0]hepto-2-ene-6-yl)-3-iodomethyl-3-butenate in 80% yield.

IR (neat) 1796, 1736 cm$^{-1}$.

NMR (δ, CDCl$_3$); 3.73 (bs, 2H), 4.90 (bs, 2H), 5.00 (s, 1H), 5.20 (s, 3H), 5.45 (s, 1H), 5.85 and 6.01 (ABq, 2H, 4 Hz), 6.7–7.4 (m, 5H), 7.34 (s, 5H).

EXAMPLE 6

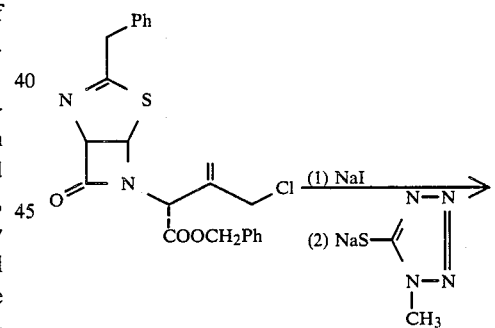

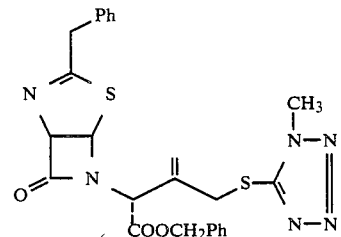

A 0.5 ml quantity of acetone was added to 26.8 mg of benzyl 2-(3-benzyl-7-oxo-4-thia-2,6-diazabicyclo[3,2,0]hepto-2-ene-6-yl)-3-chloromethyl-3-butenate to obtain a uniform solution. To the solution was added 18.2 mg of NaI and the mixture was heated to 53° C. while being stirred for 1.5 hours. The reaction mixture was cooled to room temperature and 9.2 mg of

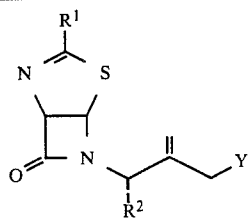

| R¹ | R² | Y | Yield (%) | IR (cm⁻¹) | NMR (δ, CDCl₃) |
|---|---|---|---|---|---|
| PhCH₂ | COOCH₂Ph | -S-C(=N-N(Ph)-N=N-)- (1-phenyl-tetrazol-5-yl-thio) | 90 | 1775, 1740 | 3.63 and 4.05 (ABq, 2H, 14Hz), 3.80 (s, 2H), 5.02 (s, 1H), 5.08 (s, 2H), 5.12 (s, 1H), 5.48 (s, 1H), 5.86 and 6.01 (ABq, 2H, 4Hz), 7.1–7.6 (m, 15H) |
| PhCH₂ | COOCH₂Ph | -S-C(=N-N=C(CH₃)S-) (5-methyl-1,3,4-thiadiazol-2-yl-thio) | 80 | 1770, 1735 | 3.60 and 3.89 (ABq, 2H, 14.5Hz), 3.83 (s, 2H), 5.00 (s, 1H), 5.14 (s, 2H), 5.20 (s, 1H), 5.35 (s, 1H), 5.85 and 5.92 (ABq, 2H, 4Hz), 7.1–7.5 (m, 10H) |
| PhCH₂ | COOCH₂Ph | -SCOC₂H₅ (S) | 85 | 1770, 1735 | 1.35 (t, 3H, 7Hz), 3.71 (s, 2H), 3.85 (s, 2H), 4.60 (q, 2H, 7Hz), 5.00 (s, 1H), 5.05 (s, 1H), 5.16 (s, 2H), 5.33 (s, 1H), 5.86 and 5.91 (ABq, 2H, 4Hz), 7.25 (s, 5H), 7.3 (s, 5H) |
| PhCH₂ | COOCH₂Ph | -SCN(CH₃)₂ (S) | 76 | 1780, 1745 | 3.35 (bs, 3H), 3.46 (bs, 3H), 3.87 (s, 2H), 4.07 (s, 2H), 5.01 (s, 1H), 5.10 (s, 1H), 5.15 (s, 2H), 5.37 (s, 1H), 5.84 and 5.88 (ABq, 2H, 4Hz), 7.26 (s, 5H), 7.31 (s, 5H) |
| PhCH₂ | COOCH₃ | -SCOC₂H₅ (S) | 89 | | Identical with the values in respect of the product obtained in Example 2 |
| PhOCH₂ | COOCH₂Ph | -SCOC₂H₅ (S) | 78 | | Identical with the values in respect of the product obtained in Example 1 |

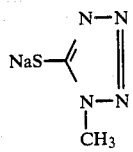

was added. The resulting mixture was stirred at room temperature for 20 minutes. The mixture was diluted with 3 ml of ethyl acetate. The dilute solution was washed with an aqueous solution of Na₂S₂O₃ and then a saturated aqueous solution of sodium chloride, dried over Na₂SO₄ and concentrated. The resulting pale yellow oily residue was subjected to silica gel column chromatography by using benzene/ethyl acetate (8:1), giving 23.8 mg of benzyl 2-(3-benzyl-7-oxo-4-thia-2,6-diazabicyclo[3,2,0]hepto-2-ene-6-yl)-3-(1-methyl-1,2,3,4-tetrazol-5-yl-thiomethyl)-3-butenate in 75% yield.

IR (neat) 1770, 1740 cm⁻¹.

NMR (δ, CDCl₃); 3.47 and 3.93 (ABq, 2H, 14.5 Hz), 3.71 (s, 3H), 3.85 (s, 2H, 4.91 (s, 1H), 5.09 (s, 2H), 5.17 (s, 1H), 5.29 (s, 1H), 5.85 and 5.93 (ABq, 2H, 4 Hz), 7.25 (s, 5H), 7.34 (s, 5H).

EXAMPLE 7

Compounds of the following formula were prepared in the same manner as in Example 6.

EXAMPLE 8

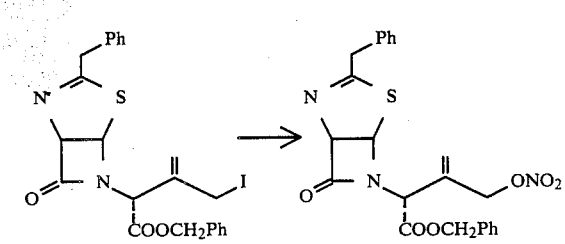

A 0.9 ml quantity of dimethyl sulfoxide was added to 103.5 mg of benzyl 2-(3-benzyl-7-oxo-4-thia-2,6-diazabicyclo[3,2,0]hepto-2-ene-6-yl)-3-iodomethyl-3-butenate to obtain a uniform solution. Thereto were added 80 mg of NaNO₃ and 40 mg of methyl methanesulfonate and they were dissolved in the solution. The reaction system was heated to 48° C. and reacted for 4 hours while being maintained at reduced pressure of 45 to 50 mmHg by a water-jet pump. The resulting reaction mixture was left to stand until it was cooled to room temperature. To the mixture was added an aqueous solution of Na₂S₂O₃ and the resultant mixture was vigorously agitated and extracted with ethyl acetate. The organic layer was washed with a saturated aqueous solution of sodium chloride and dried over Na₂SO₄ and concentrated. The yellow oily residue thus obtained was subjected to silica gel column chromatography by using benzene/ethyl acetate (15:1), giving 68.5 mg of benzyl 2-(3-benzyl-7-oxo-4-thia-2,6-diazabicyclo[3,2,0-]hepto-2-ene-6-yl)-3-nitroxymethyl-3-butenate in 76% yield.

IR (neat) 1780, 1740, 1640, 1275 cm$^{-1}$.

NMR (δ, CDCl$_3$); 3.85 (s, 2H), 4.74 (s, 2H), 5.01 (s, 1H), 5.18 (s, 2H), 5.22 (s, 1H), 5.43 (s, 1H), 5.89 and 5.93 (ABq, 2H, 4 Hz), 7.28 (s, 5H), 7.34 (s, 5H).

EXAMPLE 9

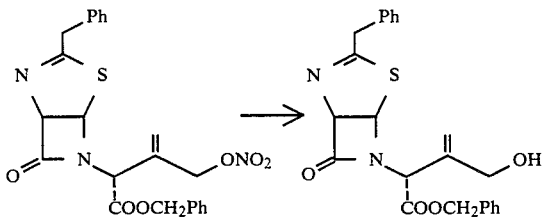

A 0.25 ml quantity of methylene chloride was added to 31.2 mg of benzyl 2-(3-benzyl-7-oxo-4-thia-2,6-diazabicyclo[3,2,0]hepto-2-ene-6-yl)-3-nitroxymethyl-3-butenate to obtain a uniform solution. To the solution was added 15 mg of zinc powder and the mixture was cooled to 0° to 5° C. Thereto was added 0.25 ml of acetic acid and the mixture was reacted while being stirred for 130 minutes. The reaction mixture was diluted with 3 ml of ethyl acetate. The dilute solution was washed with a saturated aqueous solution of NaHCO$_3$ and then a saturated aqueous solution of sodium chloride, dried over Na$_2$SO$_4$ and concentrated at reduced pressure. The pale yellow oily residue thus obtained was subjected to silica gel column chromatography by using benzene/ethyl acetate (3:1), giving 22.6 mg of benzyl 2-(3-benzyl-7-oxo-4-thia-2,6-diazabicyclo[3,2,0-]hepto-2-ene-6-yl)-3-hydroxymethyl-3-butenate in 80% yield.

IR (neat) 3380, 1770, 1740, 1150 cm$^{-1}$.

NMR (δ, CDCl$_3$); 2.12 (bs, 1H), 3.85 (s, 2H), 3.97 (s, 2H), 5.00 (s, 1H), 5.08 (s, 1H), 5.20 (s, 2H), 5.29 (s, 1H), 5.91 (s, 2H), 7.32 (s, 5H), 7.37 (s, 5H).

EXAMPLE 10

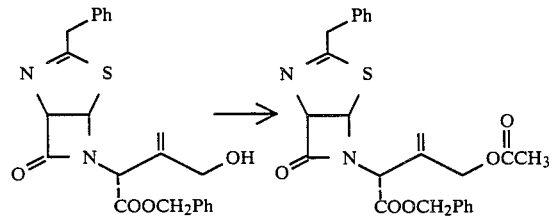

A 0.3 ml quantity of methylene chloride was added to 23.8 mg of benzyl 2-(3-benzyl-7-oxo-4-thia-2,6-diazabicyclo[3,2,0]hepto-2-ene-6-yl)-3-hydroxymethyl-3-butenate to obtain a uniform solution. The mixture was cooled to 0° to 5° C., and thereto were added 22 μl of acetic anhydride and then 12 μl of pyridine. The mixture was reacted for 12 hours. The solvent and the like were distilled off at reduced pressure by using a vaccum pump. The pale yellow oily residue thus obtained was subjected to silica gel column chromatography by using benzene/ethyl acetate (10:1), giving 24.7 mg of benzyl 2-(3-benzyl-7-oxo-4-thia-2,6-diazabicyclo[3,2,0]hepto-2-ene-6-yl)-3-acetoxymethyl-3-butenate in 94% yield.

IR (neat) 1775, 1745, 1740 (sh), 1230 cm$^{-1}$.

NMR (δ, CDCl$_3$); 2.00 (s, 3H), 3.84 (s, 2H) 4.49 (s, 2H), 5.05 (s, 2H), 5.15 (s, 2H), 5.29 (s, 1H), 5.88 (bs, 2H), 7.24 (s, 5H), 7.32 (s, 5H).

EXAMPLE 11

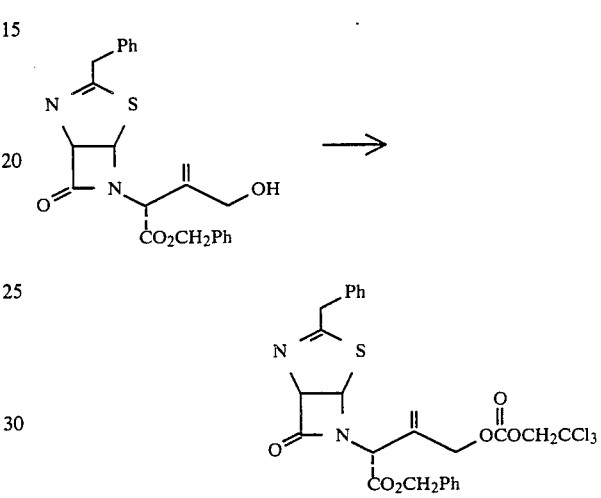

A 0.3 ml quantity of methylene chloride was added to 28.3 mg of benzyl 2-(3-benzyl-7-oxo-4-thia-2,6-diazabicyclo[3,2,0]hepto-2-ene-6-yl)-3-hydroxymethyl-3-butenate to obtain a uniform solution. The solution was cooled to 0° to 5° C. and thereto were added 14.4 μl of

and 15.6 μl of pyridine to undergo reaction for 2.5 hours. To the reaction mixture was added a 5% hydrochloric acid solution. The resulting mixture was extracted with ethyl acetate. The ethyl acetate solution thus obtained was washed with a saturated aqueous solution of sodium chloride and dried over Na$_2$SO$_4$ and the solvent was distilled off at reduced pressure. The colorless oily residue was subjected to silica gel column chromatography by using benzene/ethyl acetate (20:1), giving 30 mg of benzyl 2-(3-benzyl-7-oxo-4-thia-2,6-diazabicyclo[3,2,0]hepto-2-ene-6-yl)-3-(2,2,2-trichloroethoxycarbonyloxymethyl)-3-butenate in 75% yield.

IR (neat) 1770, 1745(sh), 1730(sh), 1235 cm$^{-1}$.

NMR (δ, CDCl$_3$); 3.85 (s, 2H), 4.10 (s, 2H), 4.23 (s, 2H), 5.04 (s, 1H), 5.16 (s, 3H), 5.37 (s, 1H), 5.84 and 5.91 (ABq, 2H, 4 Hz), 7.25 (s, 5H), 7.34 (s, 5H).

EXAMPLE 12

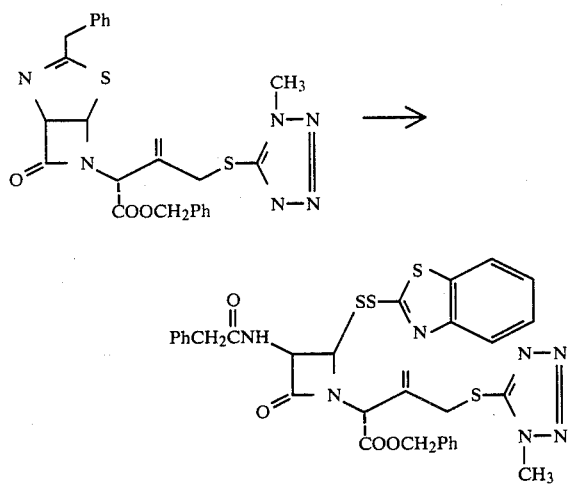

A 0.6 ml quantity of dioxane was added to 29.7 mg of benzyl 2-(3-benzyl-7-oxo-4-thia-2,6-diazabicyclo[3,2,0-]hepto-2-ene-6-yl)-3-(1-methyl-1,2,3,4-tetrazole-5-yl-thiomethyl)-3-butenate to obtain a uniform solution. Thereto was added 60 μl of a 5% hydrochloric acid solution and the mixture was reacted at room temperature for 15 minutes.

Aside from the above procedure, 2 ml of dioxane was added to 37.9 mg of 2-benzothiazolyl disulfide, and the mixture was heated in a hot-water bath to obtain a uniform solution. To the solution was added 0.14 ml of a 0.59M carbon tetrachloride solution of hydrochloric acid and the mixture was reacted for 15 minutes. The resulting reaction mixture was added to the foregoing dioxane solution, and the resulting mixture was reacted with stirring at room temperature for 5 minutes. The reaction mixture was passed through a short silica gel column using ethyl acetate and the eluate was concentrated at reduced pressure. The residue thus obtained was dissolved in benzene and the benzene was removed from the solution at reduced pressure by distillation. The residual mixture of colorless solids and colorless oily product thus obtained was subjected to silica gel column chromatography by using benzene and then benzene/ethyl acetate (4:1), giving 35.7 mg of benzyl 2-[3-phenylacetamide-4-(2-benzothiazolyldithio)-2-azetidinone-1-yl]-3-(1-methyl-1,2,3,4-tetrazole-5-yl-thiomethyl)-3-butenate in 89% yield.

IR (neat) 3280, 1780, 1740, 1670 cm$^{-1}$.

NMR(δ, CDCl$_3$); 3.69 (s, 2H), 3.74 (s, 3H), 4.19 (s, 2H), 5.10 (s, 3H), 5.23 (dd, 1H, 4.5 Hz, 8 Hz), 5.36 (s, 1H), 5.48 (s, 1H), 5.57 (d, 1H, 4.5 Hz), 6.79 (d, 1H, 8 Hz), 7.1–7.6 (m, 12H), 7.6–8.0 (m, 2H).

EXAMPLE 13

Compounds of the following formula were prepared in the same manner as in Example 12.

| R$^1$ | R$^2$ | Y | Z | Yield (%) | IR (cm$^{-1}$) | NMR (δ, CDCl$_3$) |
|---|---|---|---|---|---|---|
| PhCH$_2$ | COOCH$_2$Ph | −S−C(=N−N(Ph)−N=N)− (1-phenyl-tetrazolyl-thio) | 2-benzothiazolyl | 82 | 3280 1780 1740 1670 | 3.68 (s, 2H), 4.30 (s, 2H), 5.07 (s, 2H), 5.17 (s, 1H), 5.26 (dd, 1H, 4.5Hz, 8Hz), 5.31 (s, 1H), 5.55 (d, 1H, 4.5Hz), 5.59 (s, 1H), 6.83 (d, 1H, 8Hz), 7.17–7.6 (m, 17H), 7.6–8.0 (m, 2H) |
| PhCH$_2$ | COOCH$_2$Ph | −S−C(=N−N=C(CH$_3$)−S) (4-methylthiazolyl-thio) | 2-benzothiazolyl | 72 | 3270 1780 1740 1670 | 2.63 (s, 3H), 3.70 (s, 2H), 4.19 and 4.26 (ABq, 2H, 15Hz), 5.14 (s, 2H), 5.19 (s, 1H), 5.3–5.7 (m, 4H), 7.0–7.6 (m, 13H), 7.6–8.0 (m, 2H) |
| PhCH$_2$ | COOCH$_2$Ph | −SC(=S)OC$_2$H$_5$ | 2-benzothiazolyl | 60 | 3280 1780 1740 1670 | 1.33 (t, 3H, 7Hz), 3.64 (s, 2H), 4.01 (s, 2H), 4.56 (q, 2H, 7Hz), 5.12 (s, 2H), 5.17 (s, 2H), 5.28 (dd, 1H, 4.5Hz, 8Hz), 5.46 (s, 1H), 5.50 (d, 1H, 4.5Hz), 6.76 (d, 1H, 8Hz), 7.1–7.6 (m, 12H) |
| PhCH$_2$ | COOCH$_2$Ph | −SC(=S)N(CH$_3$)$_2$ | 2-benzothiazolyl | 45 | 3300 1780 1745 1670 | 3.31 (bs, 3H), 3.39 (bs, 3H), 3.65 (s, 2H), 4.20 and 4.55 (ABq, 2H, 15Hz), 5.13 (s, 3H), 5.25 (s, 1H), 5.29 (dd, 1H, 4.5Hz, 8Hz), 5.50 (s, 1H), 5.52 (d, 1H, 4.5Hz), 6.76(d, 1H, 8Hz), 7.2–7.6 (m, 12H), 7.6–8.0 (m, 2H) |

-continued

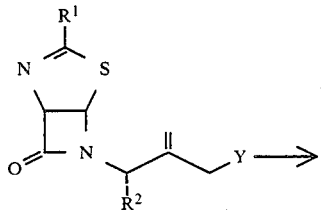

| R¹ | R² | Y | Z | Yield (%) | IR (cm⁻¹) | NMR (δ, CDCl₃) |
|---|---|---|---|---|---|---|
| PhCH₂ | COOCH₂Ph | —ONO₂ | 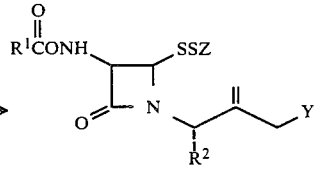 | 70 | 3280<br>1780<br>1740<br>1670<br>1640<br>1270 | 3.66 (s, 2H), 5.10 (s, 2H),<br>5.14 (s, 2H), 5.0–5.3 (m, 2H),<br>5.40 (s, 1H), 5.51 (d, 1H, 5Hz),<br>5.56 (s, 1H), 6.56 (d, 1H, 7.5Hz),<br>7.1–7.6 (m, 12H), 7.6–8.0 (m, 2H) |
| PhCH₂ | COOCH₂Ph | $-\overset{O}{\underset{\parallel}{C}}-OCH_3$ | 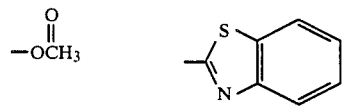 | 71 | 3280<br>1780<br>1745<br>1670<br>1235 | 2.00 (s, 3H), 3.64 (s, 2H),<br>4.70 (s, 2H), 5.11 (s, 3H),<br>5.18 (dd, 1H, 5Hz, 8Hz),<br>5.25 (s, 1H), 5.46 (s, 1H),<br>5.48 (s, 1H, 5Hz),<br>6.63 (d, 1H, 8Hz),<br>7.1–7.6 (m, 12H), 7.6–8.0 (m, 2H) |
| PhCH₂ | COOCH₃ | $-S\overset{S}{\underset{\parallel}{C}}OC_2H_5$ | 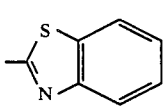 | 68 | 3280<br>1780<br>1735<br>1670 | 1.39 (t, 3H, 7Hz),<br>3.69 (s, 5H), 4.06 (s, 2H),<br>4.64 (q, 2H, 7Hz),<br>5.13 (s, 1H), 5.28 (s, 1H),<br>5.33 (dd, 1H, 4Hz, 8Hz),<br>5.51 (d, 1H, 4Hz), 5.53 (s, 1H),<br>6.81 (d, 1H, 8Hz),<br>7.1–7.6 (m, 7H), 7.6–8.0 (m, 2H) |
| PhOCH₂ | COOCH₂Ph | $-S\overset{S}{\underset{\parallel}{C}}OC_2H_5$ | 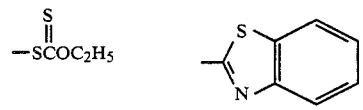 | 58 | 3300<br>1770<br>1735<br>1680 | 1.42 (t, 3H, 7Hz), 4.00 (s, 2H),<br>4.43 (bs, 2H), 4.70 (q, 2H, 7Hz),<br>5.05 (s, 1H), 5.10 (s, 1H),<br>5.25 (s, 2H), 5.39 (s, 1H),<br>5.56 (dd, 1H, 4.5Hz, 8Hz),<br>5.83 (d, 1H, 4.5Hz),<br>6.7–7.5 (m, 6H), 7.4 (s, 5H) |

EXAMPLE 14

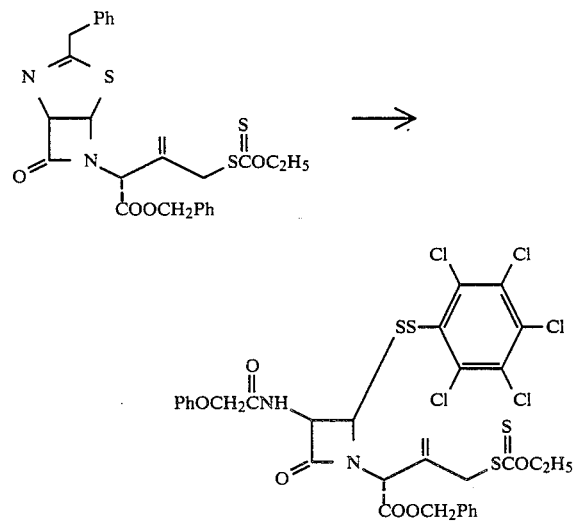

A 0.5 ml quantity of dioxane was added to 32.0 mg of benzyl 2-(3-phenoxymethyl-7-oxo-4-thia-2,6-diazabicyclo[3,2,0]hepto-2-ene-6-yl)-3-ethoxythiocarbonylthiomethyl-3-butenate to obtain a uniform solution. To the solution was added 0.09 ml of a 10% hydrochloric acid solution and the resulting mixture was reacted at room temperature for 15 minutes.

Aside from the above procedure, 1.9 ml of dioxane was added to 66.6 mg of pentachlorobenzene thiol and the mixture was heated in a hot-water bath to obtain a uniform solution. Thereto was added 0.24 ml of a 1M carbon tetrachloride of hydrochloric acid and the mixture was reacted for 15 minutes. The reaction mixture was added to the foregoing dioxane solution and the resulting mixture was reacted with stirring at room temperature for 30 minutes. The reaction mixture was passed through a short silica gel column using ethyl acetate and the eluate was concentrated at reduced pressure. The residue thus obtained was dissolved in benzene and the benzene was distilled off at reduced pressure. The residual mixture of colorless solids and pale yellow oily product thus obtained was subjected to silica gel column chromatography, using benzene and then benzene/ethyl acetate (40:1), giving 17.1 mg of benzyl 2-(3-phenoxyacetamide-4-pentachlorophenyldithio-2-azetidinone-1-yl)-3-ethoxycarbonylthiomethyl-3-butenate in 34% yield. The result of chemical analysis conducted in respect of the produce was found identical with that of the product obtained in Example 13.

EXAMPLE 15

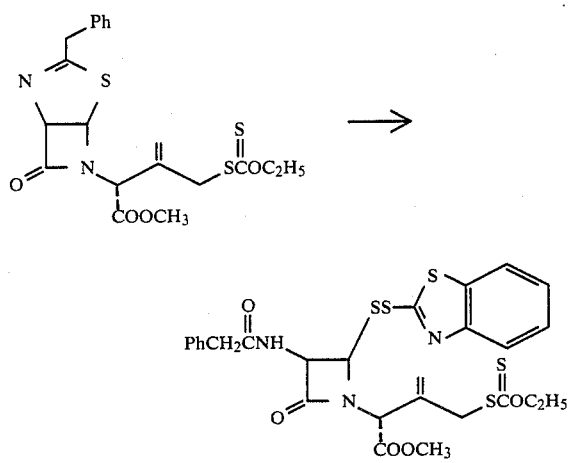

A 0.25 ml quantity of dioxane was added to 25.1 mg of methyl 2-(3-benzyl-7-oxo-4-thia-2,6-diazabicyclo[3,2,0]hepto-2-ene-6-yl)-3-ethoxycarbonylthiomethyl-3-butenate to obtain a uniform solution. To the solution was added 50 μl of water.

Aside from the above procedure, 9.4 ml of 2-mercaptobenzothiazole and 14.2 mg of iodine were dissolved in 1 ml of dioxane. The solution thus obtained was added to the foregoing dioxane solution. The mixture was reacted at room temperature for 90 minutes. The reaction mixture was diluted with 5 ml of diethyl ether and the dilute solution was washed with an aqueous solution of $Na_2S_2O_3$ and a saturated aqueous solution of sodium chloride, dried over $Na_2SO_4$ and concentrated at reduced pressure. The yellow oily residue thus obtained was subjected to silica gel column chromatography, using benzene/ethyl acetate (8:1), giving 18.2 mg of methyl 2-(3-phenylacetamido-4-(2-benzothiazolyldithio)-2-azetidinone-1-yl)-3-ethoxythiocarbonylthiomethyl-3-butenate in 52% yield. The compound thus obtained was chemically analyzed with the result identical with that of the compound obtained in Example 13.

EXAMPLE 16

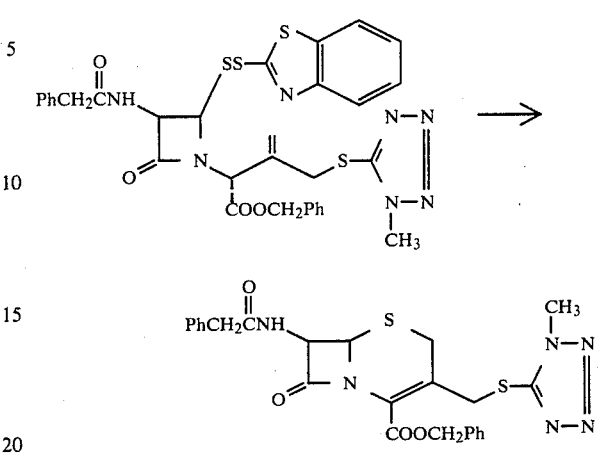

A 0.7 ml quantity of dimethylformamide was added to 35.7 mg of benzyl 2-[3-phenylacetamide-4-(2-benzothiazolyldithio)-2-azetidinone-1-yl]-3-(1-methyl-1,2,3,4-tetrazole-5-yl-thiomethyl)-3-butenate to obtain a uniform solution. To the solution cooled to −30° to −35° C. was added 23 μl of a solution (about 3.3M) prepared by forcing ammonia gas into dimethylformamide and the mixture was stirred for 15 minutes. The excess of ammonia was removed at reduced pressure by a vacuum pump from the reaction mixture which was maintained at −30° C. The solvent was distilled off while the temperature was gradually reduced to room temperature. The pale yellow oily residue thus obtained was subjected to silica gel column chromatography, using benzene and then benzene/ethyl acetate (4:1), giving 24.6 mg of benzyl 7-phenylacetamide-3-(1-methyl-1,2,3,4-tetrazole-5-yl-thiomethyl)-3-cephem-4-carboxylate in 90% yield.

NMR (δ, CDCl₃); 3.61 (s, 2H), 3.66 (s, 2H), 3.84 (s, 3H), 4.25 and 4.45 (ABq, 2H, 13 Hz), 4.90 (d, 1H, 5 Hz), 5.27 (s, 2H), 5.79 (dd, 1H, 5 Hz, 7.5 Hz), 6.35 (d, 1H, 7.5 Hz), 7.30 (s, 5H), 7.47 (s, 5H).

EXAMPLE 17

The following compounds were prepared by the same process as in Example 16.

| R¹ | R² | Y | Z | Yield (%) | NMR (δ, CDCl₃) |
|---|---|---|---|---|---|
| PhCH₂ | COOCH₂Ph | -S-C(=N-N(Ph))-N=N | 2-benzothiazolyl | 89 | 3.60 (s, 2H), 3.65 (s, 2H), 4.23 and 4.61 (ABq, 2H, 14Hz), 4.86 (d, 1H, 5Hz), 5.26 (s, 2H), 5.75 (dd, 1H, 5Hz, 7.5Hz), 6.50 (d, 1H, 7.5Hz), 7.25 (s, 5H), 7.33 (s, 5H), 7.50 (s, 5H) |
| PhCH₂ | COOCH₂Ph | -S-C(=N-N)-S-CH₃ | 2-benzothiazolyl | 86 | 2.68 (s, 3H), 3.62 (s, 4H), 4.14 and 4.64 (ABq, 2H, 14Hz), 4.90 (d, 1H, 5Hz), 5.30 (s, 2H), 5.80 (dd, 1H, 5Hz, 9Hz), 6.45 (d, 1H, 9Hz), 7.30 (s, 5H), 7.36 (s, 5H) |

-continued

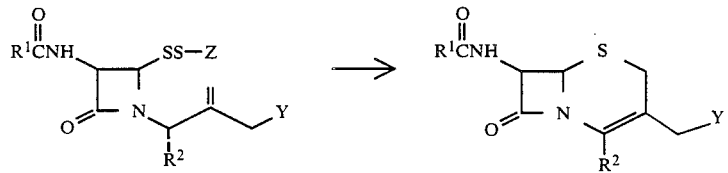

| R[1] | R[2] | Y | Z | Yield (%) | NMR (δ, CDCl₃) |
|---|---|---|---|---|---|
| PhCH₂ | COOCH₂Ph | —SCOC₂H₅ (C=S) | 2-benzothiazolyl | 82 | 1.40 (t, 3H, 7Hz), 3.44 and 3.53 (ABq, 2H, 18Hz), 3.61 (s, 2H), 4.16 and 4.48 (ABq, 2H, 14Hz), 4.64 (q, 2H, 7Hz), 4.89 (d, 1H, 4.5Hz), 5.26 (s, 2H), 5.78 (dd, 1H, 4.5Hz, 8.5Hz), 6.37 (d, 1H, 8.5Hz), 7.30 (s, 5H), 7.36 (s, 5H) |
| PhCH₂ | COOCH₂Ph | —SCN(CH₃)₂ (C=S) | 2-benzothiazolyl | 85 | 3.35 (bs, 3H), 3.56 (bs, 5H), 3.61 (s, 2H), 4.37 and 4.75 (ABq, 2H, 14Hz), 4.90 (d, 1H, 5Hz), 5.25 (s, 1H), 5.77 (dd, 1H, 5Hz, 9Hz), 6.18 (d, 1H, 9Hz), 7.30 (s, 5H), 7.37 (s, 5H) |
| PhCH₂ | COOCH₂Ph | —ONO₂ | 2-benzothiazolyl | 73 | 3.36 and 3.48 (ABq, 2H, 18Hz), 3.60 (s, 2H), 4.93 (d, 2H, 5Hz), 5.16 and 5.58 (ABq, 2H, 12Hz), 5.25 (s, 2H), 5.83 (dd, 1H, 5Hz, 8Hz), 6.33 (d, 1H, 8Hz), 7.28 (s, 5H), 7.34 (s, 5H) |
| PhCH₂ | COOCH₂Ph | —OC(O)CH₃ | 2-benzothiazolyl | 84 | 2.01 (s, 3H), 3.35 and 3.46 (ABq, 2H, 18Hz), 3.60 (s, 2H), 4.82 and 5.03 (ABq, 2H, 13Hz), 4.93 (d, 1H, 4Hz), 5.24 (s, 2H), 5.82 (dd, 1H, 4Hz, 9Hz), 6.53 (d, 1H, 9Hz), 7.30 (s, 5H), 7.37 (s, 5H) |
| PhOCH₂ | COOCH₂Ph | —S-C(=S)-N=N-C-CH₃ (thiadiazolyl) | 2-benzothiazolyl | 88 | 2.68 (s, 3H), 3.68 (s, 2H), 4.19 and 4.66 (ABq, 2H, 14Hz), 4.55 (s, 2H), 4.95 (d, 1H, 5Hz), 5.33 (s, 2H), 5.89 (dd, 1H, 5Hz, 9.5Hz), 6.7–7.7 (m, 11H) |
| PhOCH₂ | COOCH₂Ph | —S-(2-benzothiazolyl) | 2-benzothiazolyl | 92 | 3.67 (bs, 2H), 4.19 and 4.89 (ABq, 2H, 14Hz), 4.55 (s, 2H), 4.94 (d, 1H, 5Hz), 5.36 (s, 2H), 5.88 (dd, 1H, 5Hz, 10Hz), 6.7–8.1 (m, 15H) |
| PhCH₂ | COOCH₂Ph | —S-(1-methyltetrazol-5-yl) | pentachlorophenyl | 75 | 3.61 (s, 2H), 3.66 (s, 2H), 3.84 (s, 3H), 4.25 and 4.45 (ABq, 2H, 13Hz), 4.90 (d, 1H, 5Hz), 5.27 (s, 2H), 5.79 (dd, 1H, 5Hz, 7.5Hz), 6.35 (d, 1H, 7.5Hz), 7.30 (s, 5H), 7.47 (s, 5H) |

EXAMPLE 18

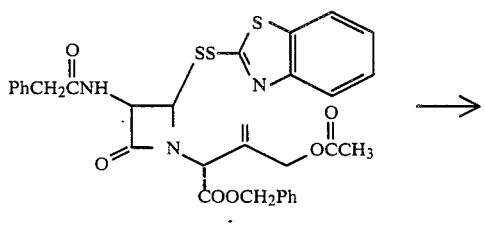

→

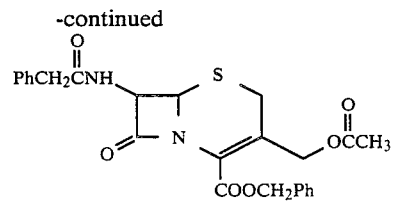

A 0.55 ml quantity of dimethylformamide was added to 43.0 mg of benzyl 2-[3-phenylacetamide-4-(2-benzothiazolyldithio)-2-azetidinone-1-yl]-3-acetoxymethyl-3- butenate to obtain a uniform solution. The solution was cooled to −25° C. and 14 μl of a 28% aqueous solution of ammonia was added thereto. The mixture was reacted with stirring for 1 hour. Five droplets of a 5% aqueous solution of hydrochloric acid were added to the reaction mixture. The resulting mixture was stirred until it was cooled to room temperature. The cooled mixture was diluted with 3 ml of ethyl acetate. The dilute solution was washed with a saturated aqueous solution of sodium chloride and dried over Na₂SO₄. The solvent was removed by distillation at reduced pressure. The pale yellow residue thus obtained was subjected to silica gel column chromatography, using benzene/ethyl acetate (10:1), giving 22.9 mg of benzyl 7-phenylacetamide-3-acetoxymethyl-3-cephem-4-carboxylate in 72% yield. The result of chemical analysis conducted in respect of the compound thus obtained was found identical with that of the compound obtained in Example 17.

EXAMPLE 19

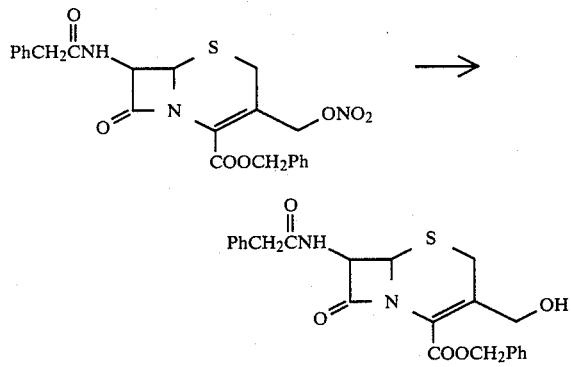

A 0.15 ml quantity of methylene chloride was added to 12.9 mg of benzyl 7-phenylacetamide-3-nitroxymethyl-3-cephem-4-carboxylate to obtain a uniform solution. Thereto was added 5.2 mg of zinc powder and the mixture was cooled to 0° to 5° C. To the mixture was added 0.15 ml of acetic acid and the resulting mixture was agitated for 135 minutes. The reaction mixture was diluted with 3 ml of ethyl acetate and the dilute solution was washed with a saturated aqueous solution of NaHCO₃ and with a saturated aqueous solution of sodium chloride and dried over Na₂SO₄. The concentration at reduced pressure of the dried product gave 10.0 mg of benzyl 7-phenylacetamide-3-hydroxymethyl-3-cephem-4-carboxylate in 85% yield.

NMR (δ, CDCl₃); 2.60 (bs, 1H), 3.52 (s, 2H), 3.61 (s, 2H), 4.02 and 4.48 (ABq, 2H, 13.5 Hz), 4.90 (d, 1H, 4 Hz), 5.25 (s, 2H), 5.81 (dd, 1H, 4 Hz, 9 Hz), 6.51 (d, 1H, 9 Hz), 7.28 (s, 5H), 7.37 (s, 5H).

What is claimed is:

1. A process for preparing a cephalosporin compound of the formula

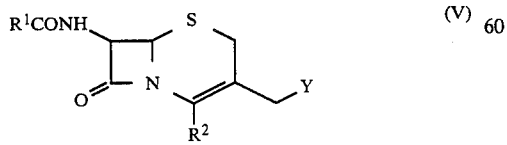

wherein R¹ represents alkyl having 1 to 4 carbon atoms; alkenyl having 2 to 6 carbon atoms; phenyl; naphthyl; phenyl substituted on the aromatic ring with one or two lower alkyls, one halogen, nitro or lower alkyloxy; benzyl; naphthylmethyl; phenylmethyl substituted on the phenyl ring with one lower alkyl, halogen, nitro or lower alkoxy; phenoxymethyl; and phenoxymethyl substituted on the phenyl ring with one lower alkyl, halogen, nitro or lower alkyloxy;

R² represents carboxyl, COOR′ or CONHR′ wherein R′ is methyl, 2,2,2-trichloroethyl, diphenylmethyl, benzyl, p-nitrobenzyl, isobutyl or tert-butyl;

Y is

wherein R³ is alkyl having 1 to 4 carbon atoms which is optionally substituted with one or three halogen atoms; or phenyl optionally substituted with one lower alkyl, halogen, nitro or lower alkoxy;

said process comprising the steps of
(1) reacting a thiazolinoazetidinone compound of the formula

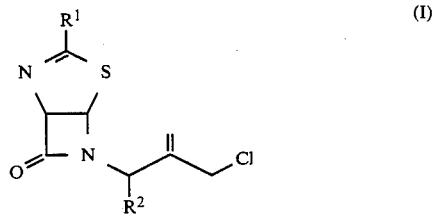

wherein R¹ and R² are as defined above with a nucleophilic reagent of the formula

wherein M is an alkali metal atom and R³ is as defined above, in an organic solvent capable of dissolving the compound of the formula (I) and the nucleophilic reagent to give a thiazolinoazetidinone compound of the formula

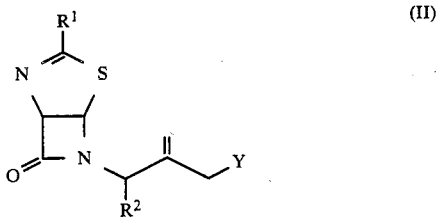

wherein R¹, R² and Y are as defined above;
(2) reacting the compound of the formula (II) in a water-containing organic solvent having a water content of about 1 to about 500 moles of water per mole of the compound of the formula (II) with a sulfur-containing compound of the formula

wherein Z represents substituted or unsubstituted aryl or residue of a substituted or unsubstituted aromatic heterocyclic ring and X represents a halogen atom to produce an azetidinone compound of the formula

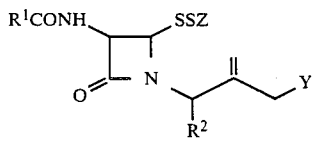

wherein $R^1$, $R^2$, Y and Z are as defined above; and (3) reacting ammonia with the compound of the formula (IV) in an inert aprotic polar solvent so that the compound of the formula (IV) is subjected to ring closure to give the compound of formula (V).

2. A process as defined in claim 1 wherein Z is phenyl optionally substituted with three or five halogen, or with one substituent selected from the group consisting of nitro, 2-pyridyl, 2-benzothiazolyl, 1,3,4-thiadiazole-2-yl and 5-methyl-1,3,4-thiadiazole-2-yl.

3. A process as defined in claim 1 wherein $R^1$ is methyl, ethyl, propyl, isopropyl, butyl, tert-butyl, allyl, butenyl, hexenyl, phenyl, naphthyl, tolyl, xylyl, p-chlorophenyl, p-nitrophenyl, p-methoxyphenyl, benzyl, naphthylmethyl, tolylmethyl, p-chlorophenylmethyl, p-nitrophenylmethyl, p-methoxyphenylmethyl, phenoxymethyl, tolyloxymethyl, p-chlorophenoxymethyl, p-nitrophenoxymethyl or p-methoxyphenoxymethyl.

* * * * *